(12) United States Patent
Polonka et al.

(10) Patent No.: US 8,206,730 B2
(45) Date of Patent: *Jun. 26, 2012

(54) SUNSCREEN COMPOSITE PARTICLES AND POROUS PARTICLES IN COSMETIC COMPOSTIONS

(75) Inventors: Jack Polonka, Peekskill, NY (US); John Brian Bartolone, Bridgeport, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 466 days.

This patent is subject to a terminal disclaimer.

(21) Appl. No.: 12/164,137

(22) Filed: Jun. 30, 2008

(65) Prior Publication Data

US 2009/0324654 A1    Dec. 31, 2009

(51) Int. Cl.
*A61K 8/02* (2006.01)
*A61K 8/00* (2006.01)
*A61K 8/18* (2006.01)
*A61K 47/30* (2006.01)
*A61Q 17/04* (2006.01)

(52) U.S. Cl. ............... 424/401; 424/59; 514/772.3

(58) Field of Classification Search ............ 424/401, 424/59
See application file for complete search history.

(56) References Cited

U.S. PATENT DOCUMENTS

| | | | |
|---|---|---|---|
| 3,895,104 A | 7/1975 | Karg | |
| 4,731,242 A | 3/1988 | Palinczar | |
| 5,264,207 A | 11/1993 | Bommelaer et al. | |
| 5,733,531 A | 3/1998 | Mitchnick et al. | |
| 5,783,657 A | 7/1998 | Pavlin et al. | |
| 5,972,359 A | 10/1999 | Sine et al. | |
| 5,997,890 A | 12/1999 | Sine et al. | |
| 5,998,570 A | 12/1999 | Pavlin et al. | |
| 6,036,945 A | 3/2000 | Deblasi et al. | |
| 6,174,533 B1 | 1/2001 | SaNogueira, Jr. et al. | |
| 6,242,509 B1 | 6/2001 | Berger et al. | |
| 6,280,710 B1 | 8/2001 | Deblasi et al. | |
| 6,368,577 B1 * | 4/2002 | Kropf et al. ............ 424/59 | |
| 6,399,713 B1 | 6/2002 | MacQueen et al. | |
| 6,402,408 B1 | 6/2002 | Ferrari | |
| 6,492,458 B1 | 12/2002 | Pavlin | |
| 6,495,123 B1 | 12/2002 | Faryniarz et al. | |
| 6,552,160 B2 | 4/2003 | Pavlin | |
| 6,592,857 B2 * | 7/2003 | Lawson et al. ........ 424/70.122 | |
| 6,685,966 B1 | 2/2004 | Dominique et al. | |
| 6,835,399 B2 | 12/2004 | Collin | |
| 6,870,011 B2 | 3/2005 | MacQueen et al. | |
| 6,875,245 B2 | 4/2005 | Pavlin | |
| 7,253,249 B2 | 8/2007 | Pavlin | |
| 7,264,795 B2 | 9/2007 | Pflucker et al. | |
| 7,329,719 B2 | 2/2008 | Pavlin | |
| 7,351,418 B2 | 4/2008 | Collin | |
| 2005/0163730 A1 | 7/2005 | Rosevear et al. | |
| 2005/0163813 A1 | 7/2005 | Kosbach et al. | |
| 2005/0197479 A1 | 9/2005 | Pavlin | |
| 2005/0249684 A1 | 11/2005 | Dobkowski et al. | |
| 2005/0276833 A1 | 12/2005 | Fowler | |
| 2006/0099168 A1 | 5/2006 | Corzani et al. | |
| 2006/0115504 A1 | 6/2006 | Loyen et al. | |
| 2006/0280763 A1 | 12/2006 | Yoshida et al. | |
| 2006/0292095 A1 * | 12/2006 | Biatry et al. ............ 424/59 | |
| 2007/0212315 A1 | 9/2007 | Pastor et al. | |
| 2008/0115846 A1 | 5/2008 | Josso et al. | |
| 2008/0311064 A1 * | 12/2008 | Lei et al. ............ 424/70.11 | |
| 2009/0016971 A1 | 1/2009 | Gaudry et al. | |

FOREIGN PATENT DOCUMENTS

| | | |
|---|---|---|
| EP | 0 810 181 A2 | 12/1997 |
| EP | 0 904 768 A1 | 9/1998 |
| EP | 1 072 651 A1 | 1/2001 |
| EP | 1 123 697 A1 | 8/2001 |
| EP | 1 388 550 A1 | 8/2003 |
| EP | 1 475 078 A1 | 5/2004 |
| EP | 1 642 924 A1 | 9/2005 |
| EP | 1 661 546 A1 | 5/2006 |
| EP | 1 723 943 A1 | 11/2006 |
| EP | 1 813 266 A1 | 12/2006 |
| EP | 1 813 266 A1 | 8/2007 |
| EP | 2 005 940 A2 | 6/2008 |
| GB | 2 166 107 A | 4/1986 |
| WO | 01/87847 A2 | 11/2001 |
| WO | 2008/018644 A1 | 2/2008 |
| WO | 2009/007264 A2 | 1/2009 |

OTHER PUBLICATIONS

PCT International Search Report PCT/EP2009/057150; International Filing Date Jun. 10, 2009.
Co-Pending Application: Polonka et al.; Entitled: Sunscreen Composite Particles in Cosmetic Compostions.
Co-Pending Application: Polonka et al.; Entitled: Sunscreen Composite Particles Dispersed in Water-In-Oil Cosmetic Compostions.
Co-Pending Application: Polonka et al.; Entitled: Sunscreen Formula Vanishing Cream.

* cited by examiner

*Primary Examiner* — Sreeni Padmanabhan
*Assistant Examiner* — Layla Soroush
(74) *Attorney, Agent, or Firm* — Milton L. Honig

(57) ABSTRACT

A cosmetic composition is provided which includes composite particles of a sunscreen agent and a condensation polymerized polyamide binder, a water-insoluble powdered polymer of porous particles having an Oil Absorbance (castor oil) Value ranging from about 90 to about 500 ml/100 gm, and a cosmetically acceptable carrier. The composition exhibits an excellent soft focus property to hide skin imperfections, and retains relatively high SPF photoprotection.

9 Claims, No Drawings

SUNSCREEN COMPOSITE PARTICLES AND POROUS PARTICLES IN COSMETIC COMPOSTIONS

BACKGROUND OF THE INVENTION

1. Field of the Invention

The invention concerns cosmetic sunscreen compositions delivering UV protection and also soft focus properties.

2. The Related Art

Ultraviolet radiation can be damaging to skin. Immediate damage may be in the form of erythema. More long term is the concern of initiating cancerous growth. For these reasons, photoprotective agents known as sunscreens have been incorporated into cosmetic products.

Facial cosmetics desirably deliver not only photoprotection but also function to enhance overall skin appearance. Most persons have facial imperfections. These may include uneven tone, enlarged pores, fine lines and wrinkles.

Soft focus is an effect which can hide imperfect skin. Incoming light is distorted by scattering (lensing). Particulate components of the cosmetic operate as lenses to bend and twist light into a variety of directions.

U.S. Pat. No. 5,997,890 (Sine et al.), U.S. Pat. No. 5,972,359 (Sine et al.), and U.S. Pat. No. 6,174,533 B1 (SaNogueira, Jr.) are all directed to topical compositions to provide good coverage of skin imperfections. The solution proposed by these documents is the use of a metal oxide with a refractive index of at least about 2 and a neat primary particle size of from about 100 to about 300 nm. Preferred particulates are titanium dioxide, zirconium oxide and zinc oxide.

U.S. Pat. No. 6,495,123 B1 (Faryniarz et al.) discloses cosmetic compositions which include an organic sunscreen agent and water-insoluble powdered polymer formed of porous particles. The polymeric powders are utilized to modify the tacky skinfeel normally associated with the organic sunscreen agents.

Organic sunscreen agents can interfere with soft focus properties of a cosmetic formulation. Consequently, there is a challenge to provide cosmetics with a strong soft focus effect while maintaining a relatively high degree of photoprotective benefits for the composition.

SUMMARY OF THE INVENTION

A cosmetic composition is provided which includes:
(i) from about 0.1 to about 20% by weight of composite particles formed of an organic sunscreen agent and a condensation polymerized polyamide in a relative weight ratio of about 5:1 to about 1:10;
(ii) from about 0.01 to about 10% by weight of water-insoluble powdered polymer formed as porous particles having an Oil Absorbance (castor oil) value ranging from about 90 to about 500 ml/100 gm; and
(iii) a cosmetically acceptable carrier.

DETAILED DESCRIPTION OF THE INVENTION

Now it has been found that a soft focus effect for hiding skin blemishes can co-exist with a sunscreen agent that can deliver a relatively high sunscreen protection factor (SPF). The invention requires the presence of special sunscreen composite particles in combination with water-insoluble polymeric powdered porous particles. Composite particles of the present invention are formed of organic sunscreen agent and a binder which is a condensation polymerized polyamide, especially a polyalkyleneoxypolyamide referred to as a "PAOPA Resin" or an ester-terminated poly(ester-amide) referred to as "ETPEA Resin".

Relative weight ratio of organic sunscreen agent to polyamide may range from about 5:1 to 1:10, preferably from about 3:1 to about 1:8, more preferably from about 2:1 to about 1:7, optimally from about 1:1 to about 1:3. Amounts of the polyamide may range from about 10% to about 99.5% by weight of the composite particles. More preferably weight of the polyamide may range from about 30% to about 98%, optimally from about 50 to about 85% by weight of the composite particles. Amounts of the sunscreen agent may range from about 0.5 to about 90%, preferably from about 2 to about 70%, optimally from about 30 to about 50% by weight of the composite particles.

Amounts of the composite particles within the cosmetic composition may range from about 0.1 to about 30%, preferably from about 2 to about 15%, optimally from about 4 to about 10% by weight of the cosmetic composition.

Average particle size of the composite particles may range from about 10 to about 2,000 nm, preferably from about 100 to about 1,500 nm, and optimally from about 200 to about 1000 nm.

Sunscreen Composite Particles

Sunscreen particles of the present invention are formed as a composite of an organic sunscreen agent and a binder which is a condensation polymerization formed polyamide. Ester-terminated polyamides are most useful. Two examples are polyalkyleneoxypolyamide (PAOPA) and ester-terminated poly(ester-amide) (ETPEA) resins.

The polyalkyleneoxypolyamide resins useful herein are outlined in U.S. Pat. No. 6,492,458 B1 herein incorporated by reference. These PAOPA materials may be prepared by combining reactants comprising a monocarboxylic acid compound, a diamine compound, and a dibasic acid. Specifics of these reactants are described hereinbelow. Commercially the resins are available from the Arizona Chemical Company under the trademark Sylvaclear™ PA 1200V, designated by a INCI nomenclature as Polyamide-3.

Exemplary monocarboxylic acids of the formula $R^1$—COOH include, without limitation, stearic acid ($C_{18}$), 1-eicosanoic acid ($C_{20}$), 1-docasanoic acid ($C_{22}$, also known as behenic acid), dotricontanoic acid ($C_{32}$), tetratriacontanoic acid ($C_{34}$), pentatriacontanoic acid ($C_{35}$), tetracontanoic acid ($C_{40}$), tetraacontanioc acid ($C_{44}$), dopentaacontanoic acid ($C_{54}$), tetrahexaacontanoic acid ($C_{64}$), and dohexaacontanoic acid ($C_{72}$). These monocarboxylic acids are available from many commercial suppliers, including Aldrich Chemical (Milwaukee, Wis.; www.sigma-aldrich.com).

Another suitable monocarboxylic acid is the oxidized (specifically, carboxyl terminated) polyethylene materials sold by Baker-Petrolite (Sugar Land, Tex.; www.bakerhughes.com/bapt/; division of Baker Hughes; www.bakerhughes.com) as their UNICID™ acids. UNICID™ acids are fully saturated, linear carboxylic acids with average carbon chain lengths ranging from C24 to C50. Acid values for UNICID™ acids vary from 60 to 115.

Still other suitable monocarboxylic acids are the alpha-branched carboxylic acids prepared by oxidizing higher molecular weight Guerbet alcohols. Such products are available from Jarchem Industries Inc. (Newark, N.J.; www.jarchem.com) as their JARIC™ acids. JARIC™ I-36 acid is a suitable monocarboxylic acid for the resins of this invention.

The diamine reactant has two amine groups, both of which are preferably primary amines, and is represented by the formula HN($R^{2a}$)—$R^2$—N($R^{2a}$)H. $R^{2a}$ is preferably hydrogen, but may also be an alkyl group or may also join together with $R^2$ or another $R^{2a}$ to form a heterocyclic structure. A preferred diamine is ethylene diamine, i.e., a diamine wherein $R^{2a}$ is hydrogen and $R^2$ is —$CH_2CH_2$—.

Diamines other than ethylene diamine may be referred to herein as co-diamines. When present, co-diamines are preferably used in a minor amount compared to the ethylene diamine.

Exemplary co-diamines include 1,2-diaminopropane, 1,3-diaminopropane, 1,4-diaminobutane, 1,2-diamino-2-methylpropane, 1,3-diaminopentane, 1,5-diaminopentane, 2,3-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexandeiamine, 1,9-diaminononane, 1,10-diaminodecane, 1,12-diaminododecane, diaminophenanthrene (all isomers, including 9,10), 4,4'-methylenebis(cyclohexylamine), 2,7-diaminofluorene, phenylene diamine (1,3; 1,3 and/or 1,4 isomers), adamantane diamine, 2,4,6-trimethyl-1,3-phenylenediamine, 1,3-cyclohexanebis(methylamine), 1,8-diamino-p-menthane, 2,3,5,6-tetramethyl-1,4-phenylenediamine, diaminoaphthalene (all isomers, including 1,5; 1,8; and 2,3) and 4-amino-2,2,6,6-tetramethylpiperidine.

Suitable aromatic co-diamines (by which is meant molecules having two reactive, preferably primary amine groups (—$NH_2$) and at least one aromatic ring ("Ar") include xylene diamine and naphthalene diamine (all isomers).

Exemplary polyalkylene oxide-based co-diamines include without limitation, the JEFFAMINE® diamines, i.e., poly(alkyleneoxy)diamines from Huntsman Chemical (Salt Lake City, Utah), also known as polyether diamines. Preferred polyalkylene oxide-containing co-diamines are the JEFFAMINE® ED, XTJ and D series diamines.

In certain embodiments, the polyamide resins of the invention are prepared from co-diamine, where the co-diamine is selected from 1,6-hexanediamine, xylenediamine, 1,2-propanediamine, 2-methylpentamethylenediamine, and 1,12-dodecanediamine. Suitable diamines of the present invention are available from a number of commercial sources including Aldrich (Milwaukee, Wis.); EM Industries, Inc. (Hawthorne, N.Y.); Lancaster Synthesis, Inc. (Windham, N.H.) and Spectrum Quality Product, Inc. (New Brunswisk, N.J.).

The dibasic acid is an organic molecule containing two carboxylic acid groups or reactive equivalent thereof. A preferred dibasic acid is polymerized fatty acid, and in particular the dimer acid component of polymerized fatty acid. Polymerized fatty acid is typically a mixture of structures, including dimer acid and trimer acid, where individual dimer acids may be saturated, unsaturatred, cyclic, acyclic, and combinations thereof. Polymerized fatty acid is typically formed by heating long-chain unsaturated fatty acids, e.g., $C_{18}$ monocarboxylic acids, to about 200-250° C. in the presence of a clay catalyst in order that the fatty acids polymerize. The product typically comprises dimer acid, i.e. $C_{36}$ dicarboxylic acid formed by dimerization of the fatty acid, and trimer acid, i.e., $C_{54}$ tricarboxylic acid formed by trimerization of the fatty acid. A more detailed discussion of fatty acid polymerization may be found in U.S. Pat. No. 3,157,681.

Because fatty acid polymerization typically forms much more dimer acid than trimer acid, those skilled in the art may often refer to polymerized fatty acid as dimer acid, even though some trimer acid, and even higher polymerization products, may be present with the dimer acid. It is preferred that the polymerized fatty acid contain less than about 20 weight percent of trimer acid, based on the total weight of the polymerized fatty acid, and that the dimer acid constitute at least about 80 weight percent of the polymerized fatty acid. More preferably, the dimer acid constitutes essentially all of the polymerized fatty acid.

Typical unsaturated fatty acids used to form polymerized fatty acid include oleic acid, linoleic acid and linolenic acid. Tall oil fatty acid, which is a mixture containing long-chain unsaturated fatty acids obtained as a byproduct of the wood pulping process, is preferred for preparing polymerized fatty acid.

Polymerized fatty acid may be hydrogenated prior to being used in the resin-forming reaction. Hydrogenation tends to provide for a slightly higher melting point and greater oxidative and color stability.

Polymerized fatty acid, dimer acid, and hydrogenated versions thereof may be obtained from a number of commercial suppliers. For example, Arizona Chemical (Jacksonville, Fla.) sells polymerized fatty acid under their UNDYME® trademark.

In addition to polymerized fatty acid, or reactive equivalents thereof, the dibasic acid may comprise a co-diacid. An exemplary co-diacid is a so-called "linear" diacid of the formula HOOC—$R^1$—COOH wherein $R^1$ is a linear $C_{4-17}$ hydrocarbon group, and more preferably is a linear $C_{6-8}$ hydrocarbon group. Linear co-diacids suitable for the present invention include 1,6-hexanedioic acid (adipic acid), 1,7-heptanedioic acid (pimelic acid), 1-8-octanediolc acid (suberic acid), 1,9-nonanedioic acid (azelaic acid), 1,10-decanedioic acid (sebacic acid), 1,11-undecanedioic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid).

Another exemplary co-diacid is the reaction product of acrylic or methacrylic acid (or the ester thereof, with a subsequent hydrolysis step to form an acid) and an unsaturated fatty acid. For example, a $C_{21}$ diacid of this type may be formed by reacting acrylic acid with a $C_{18}$ unsaturated fatty acid (e.g., oleic acid), where an ene-reaction presumably occurs between the reactants. An exemplary $C_2$, diacid is commercially available from Westvaco Corporation, Chemical Division, Charleston Heights, S.C. as their product number 1550.

Aromatic diacids may be used as the co-diacid. An "aromatic diacid" as used herein is a molecule having two carboxylic acid groups (—COOH) or reactive equivalents thereof (e.g., acid chloride (—COCl) or ester (—COOR) and at least one aromatic ring ("Ar"). Phthalic acids, e.g., isophthalic acid and terephthalic acid, are exemplary aromatic diacids.

In one aspect, the resin is prepared with co-diacid and the co-diacid is selected from 1,4-cyclohexane dicarboxylic acid, isophthalic acid, adipic acid, azeleic acid, sebacic acid, and dodecandioic acid.

A second class of polyamides useful for this invention are the ester-terminated poly(ester-amide) resins. These are prepared by reacting components comprising dibasic acid, diamine, polyol and monoalcohol, wherein at least 50 equivalent percent of the dibasic acid comprises polymerized fatty acid; and at least 50 equivalent percent of the diamine comprises ethylene diamine. Typical dibasic acids, and diamines have already been described hereinabove.

A further constituent of the ester-terminated poly(ester-amide) resins are the monoalcohol reactants. The monoalcohol may be represented by the formula $R^3$—OH, wherein $R^3$ is preferably a hydrocarbon group having at least ten carbon atoms. Thus, the monoalcohol can also be described as a monohydric alcohol. In one aspect, $R^3$ is a $C_{10-30}$ hydrocarbon, preferably a $C_{12-24}$ hydrocarbon, still more preferably is a $C_{16-22}$ hydrocarbon, and yet still more preferably is a $C_{18}$ hydrocarbon. Preferably, $R^3$ is linear, with the hydroxyl group located on a terminal carbon atoms, i.e., the monoalcohol is a primary monoalcohol. Thus, 1-dodecanol, 1-tetradecanol, 1-hexadecanol (cetyl alcohol), 1-octadecanol (stearyl alcohol), 1-eicosanol (arachidyl alcohol) and 1-docosanol (behenyl alcohol) are preferred monoalcohols for preparing polyamide resin binders of the invention.

Another suitable monoalcohol reactant is a so-called Guerbet alcohol. Guerbet alcohols have the general formula H—C(Ra)(Rb)—$CH_2$—OH wherein Ra and Rb may be the same or different and preferably represent a $C_{6-12}$ hydrocarbon group.

Another suitable monoalcohol reactant is a linear wax alcohol. Suitable linear wax alcohols are commercially available from, e.g., Petrolite Corporation (Tulsa, Okla.) under their UNILIN® trademark. These wax alcohols are typically a blend of linear alcohols having at least about 20 carbon atoms, and more typically at least about 24 carbon atoms.

A final ingredient necessary in preparing an ETPEA resin of the present invention is polyol, which may also be referred to as polyhydric alcohol. The polyol is of the formula $R^4(OH)_n$ wherein $R^4$ is an n-valent organic group. For instance, $R^4$ may be a $C_2$-$C_{20}$ organic group without hydroxyl substitution. As another example, $R^4$ may be a hydrocarbon. Typically, n is selected from 2, 3, 4, 5 and 6. Suitable polyols for use in preparing an ETPEA resin of the present invention include ethylene glycol, propylene glycol, butylene glycol, glycerol, trimethylolpropane, pentaerythritol, neopentyl glycol, tris(hydroxylmethyl)methanol, di-pentaerythritol, and tri-pentaerthyritol.

Preparation and description of the ETPEA resins are found in U.S. Pat. No. 7,329,719 B2 herein incorporated by reference. Commercially these resins are available from the Arizona Chemical Company under the trademark Sylvaclear AF 1900V. We have found that these resins are easily intimately mixed with octylmethoxycinnamate (OMC) or other organic sunscreens to form a composite particulate with photoprotective activity.

Sunscreen agents can either be dispersed throughout the polyamide resin binder or can be formed as a core surrounded by binder. Dispersal throughout the binder is preferred.

Sunscreen agents according to this invention will have at least one chromophoric group absorbing within the ultraviolet ranging from 290 to 400 nm. Chromophoric organic sunscreen agents may be divided into the following categories (with specific examples) including: n-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl)ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoyl methane; Etocrylene; and 4-isopropyl-dibenzoylmethane).

Particularly useful sunscreen agents are: 2-ethylhexyl p-methoxycinnamate, 4,4'-t-butyl methoxydibenzoylmethane, 2-hydroxy-4-methoxybenzophenone (known also as Benzophenone-3), octyidimethyl p-aminobenzoic acid, digalloyltrioleate, 2,2-dihydroxy-4-methoxybenzophenone, ethyl 4-[bis(hydroxypropyl)]aminobenzoate, 2-ethyl hexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid, 4-methylbenzylidene camphor, bis-ethylhexyloxyphenol methoxyphenol triazine, methylene bis-benzotriazolyl tetramethyl butyl phenol, dimethicodiethylbenzal malonate, isoamyl methoxycinnamate, octyl triazone, terephthalidene dicamphor sulfonic acid and mixtures thereof.

Cosmetic compositions of this invention may not only have sunscreen agent held within the composite particles but also an amount of sunscreen agent may be formulated free of binder within the composition. When present external of the composite, the sunscreen agent may be available in amounts from about 0.1 to about 25%, particularly from about 2 to about 15% by weight of the composition. Some preferred embodiments of this invention may be formulated without any sunscreen agent external to the composites or with only a relatively small amount of such material. For instance, external sunscreen agent may range in amount from about 0 to 5%, preferably from 0.01 to 2%, and possibly from 0.01 to 0.8% by weight of the composition.

Polymeric Powdered Porous Particles

A further element of compositions according to the present invention is that of a water-insoluble material in the form of polymeric porous particles. By the term "porous" is meant an open or closed cell structure. Preferably the particles are not hollow beads. Average particle size may range from about 0.1 to about 100, preferably from about 1 to about 50, more preferably greater than 5 and especially from 5 to about 15, optimally from about 6 to about 10 micron. Organic polymers or copolymers are the preferred materials and can be formed from monomers including the acid, salt or ester forms of acrylic acid, methacrylic acid, methylacrylate, ethylacrylate, ethylene, propylene, vinylidene chloride, acrylonitrile, maleic acid, vinyl pyrrolidone, styrene, butadiene and mixtures thereof. The polymers are especially useful in cross-linked form. Cells of the porous particles may be filled by a gas which can be air, nitrogen or a hydrocarbon. Oil Absorbance (castor oil) is a measure of porosity and may range from about 90 to about 500, preferably from about 100 to about 200, optimally from about 120 to about 180 ml/100 grams. Density of the particles may range from about 0.08 to 0.55, preferably from about 0.15 to 0.48 $g/cm^3$.

Illustrative porous polymers include polymethyl methacrylate and cross-linked polystyrene. Most preferred is polymethyl methacrylate available as Ganzpearl® 820 from Presperse, Inc., Piscataway, N.J., known also by its INCI name of Methyl Methacrylate Crosspolymer.

Amounts of the water-insoluble polymeric porous particles may range from about 0.01 to about 10%, preferably from about 0.1 to about 5%, optimally from about 0.3 to about 2% by weight of the composition.

Cosmetically Acceptable Carrier

Compositions of the present invention will include a cosmetically acceptable carrier. The carrier may be a liquid or solid material. Carriers may be present in amounts ranging from about 5 to about 98%, preferably from about 20 to about 95%, optimally from about 40 to about 80% by weight of the cosmetic compositions. Water is the most common carrier for this invention. Oily carriers in the presence of water and an emulsifier will form emulsion systems as carriers. These systems may either be water-in-oil or oil-in-water emulsions. Besides water, suitable carrier classes include silicones, polyhydric alcohols, fatty alcohols, hydrocarbons, triglycerides and thickening powders.

Silicones when present may range from about 5% to about 60%, more preferably from about 5% to about 40%, by weight of the composition. These silicones may be organic, silicone-containing or fluorine-containing, volatile or non-volatile, polar or non-polar.

Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids, GE 7207 and 7158 (commercially available from G.E. Silicones) and SWS-03314 (commercially available from SWS Silicones Corp.

Hydrocarbons may be useful as cosmetically acceptable carriers for compositions of this invention. They may include mineral oil, petrolatum and polyalpha-olefins. Examples of preferred volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals).

Polyhydric alcohols may serve as carriers. Illustrative of this group are propylyene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol and mixtures thereof. Most preferred is glycerol known also as glycerin.

Fatty alcohols may also be useful carriers. The term "fatty" refers to carbon chain lengths ranging from 10 to 30 carbon atoms. Illustrative of this category are lauryl alcohol, cetyl alcohol, stearyl alcohol, isostearyl alcohol and combinations thereof.

Triglycerides are another group of materials useful as carriers. Illustrative but not limiting are sunflower seed oil, cotton oil, canola oil, soybean oil, castor oil, borage oil, olive oil, shea butter, jojoba oil and mixtures thereof. Mono- and diglycerides may also be useful. Illustrative of these categories are glyceryl monostearate and glyceryl distearate.

The carriers can comprise one or more thickening agents, preferably from about 0.05% to about 10%, more preferably from about 0.1% to about 5%, and even more preferably from about 0.25% to about 4%, by weight for the composition. Nonlimiting classes of thickening agents include those selected from the group consisting of:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the Carbomers, which are homopolymers of acrylic acid crosslinked with allyl ethers of sucrose or pentaerytritol. The Carbomers are available as the Carbopol® 900 series from Noveon Corporation (e.g. Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytriotol. These copolymers are known as Acrylates/$C_{10-30}$ Alkyl Acrylate Crosspolymers and are commercially available as Carbopol® 1342, Carbopol® 1382, Ultrez® 21, Pemulen® TR-1, and Pemulen® TR-2, from Noveon Corporation.

b. Taurate Polymers

The compositions of the present invention can optionally comprise crosslinked taurate polymers useful as thickeners or gelling agents including anionic, cationic and nonionic polymers. Examples include Hydroxyethyl Acrylate/Sodium Acryloyldimethyl Taurate (e.g. Simulgel® NS and INS100), Acrylate/Sodium Acryloyidimethyl Taurate (e.g. Simulgel® EG), Sodium Acryloyldimethyl Taurate (e.g. Simulgel® 800) and Ammonium Acryloyldimethyl TaurateNinyl Pyrrolidone (e.g. Aristoflex® AVC).

c. Polyacrylamide Polymers

The compositions of the present invention can optionally comprise vinyl polymerized polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the tradename Sepigel® 305 from Seppic Corporation.

Other free-radical polymerized polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d. Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

e. Gums and Clays

Other thickening and gelling agents useful herein include materials that are primarily derived from natural sources. Nonlimiting examples include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, laponite, bentonite, hyaluronic acid, hydrated silica, hydroxypropyl chitosan, hydroxypropyl guar, karaya gum, kelp, locust bean gum, natto gum, potassium carrageenan, propylene glycol alginate, sclerotium gum, sodium carboxymethyl dextran, sodium carrageenan, tragacanth gum, xanthan gum, and mixtures thereof.

Other Optional Components

The composition of the present invention may contain a variety of components to enhance physical properties and performance.

The optional components, when incorporated into the composition, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these classes include: abrasives, absorbents, aesthetic components such as fragrances, colorants, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents, antioxidants, biological additives, buffering agents, bulking agents, chelating agents, chemical additives, cosmetic astringents, cosmetic biocides, denaturants, drug astringents, external analgesics, film forming polymers, opacifying agents, pH adjusters, propellants, reducing agents, sequestrants, skin bleaching and lightening agents, skin conditioning agents, skin soothing and/or healing agents and derivatives, skin treating agents and vitamins and derivatives thereof.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

The compositions of the present invention may contain one or more particulate materials. Nonlimiting examples of particulate materials include colored and uncolored pigments, interference pigments, inorganic powders, organic powders; composite powders, optical brightener particles, and combinations thereof. Particulate materials may be present from about 0.01% to about 20%, more preferably from about 0.05% to about 10%, still more preferably from about 0.1% to about 5%, by weight of the composition.

Particulate materials useful herein include but are not limited to bismuth oxychloride, sericite, mica, mica treated with barium sulfate or titanium dioxide, zeolite, kaolin, silica, boron nitride, lauroyl lysine, nylon, talc, styrene, polystyrene, ethylene/acrylic acid copolymer, aluminum oxide, barium sulfate, calcium carbonate, cellulose acetate, PTFE, starch, modified starches, silk, glass, and mixtures thereof. Preferred organic powders/fillers include polymeric particles chosen from the methylsilsesquioxane resin microspheres such as those sold by Toshiba Silicone under the name Tospearl 145A; the spherical particles of crosslinked polydimethylsiloxanes, especially such as those sold by Dow Corning Toray Silicone under the name Trefil E 506C or Trefil E 505C; spherical particles of polyamide and more specifically Nylon 12, especially such as those sold by Atochem under the name Orgasol 2002N Nat C05; polystyrene microspheres such as those sold by Dyno Particles under the name Dynospheres; ethylene acrylate copolymer sold by Kobo under the name FloBead EA209; PTFE; polypropylene; aluminum starch octenylsuccinate such as sold by National Starch under the name Dry Flo; microspheres of polyethylene such as those sold by Equistar under the name of Microthene FN510-00; silicone resin; platelet shaped powder made from L-lauroyl lysine, and mixtures thereof. Especially preferred are spherical powders with an average primary particle size from 0.1 to 75 microns, preferably from 0.2 to 30 microns.

A safe and effective amount of an anti-oxidant/radical scavenger may be added in amounts from about 0.01% to about 10%, more preferably from about 0.1% to about 5% by weight of the composition.

Anti-oxidants/radical scavengers may be employed such as ascorbic acid (vitamin C) and its salts, ascorbyl esters of fatty acids, ascorbic acid derivatives (e.g. magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolor®), amines (e.g. N,N-diethylhydroxylamine, amino-guanidine), nordihydroguaiaretic acid, bioflavonoids, amino acids, silymarin, tea extracts, and grape skin/seed extracts. Preferred anti-oxidants/radical scavengers are selected from esters of tocopherol, more preferably tocopherol acetate.

The compositions of the present invention may optionally comprise a flavonoid compound. Flavonoids are disclosed in U.S. Pat. Nos. 5,686,082 and 5,686,367 herein incorporated by reference. Examples of flavonoids particularly suitable flavones, isoflavones, coumarins, chromones, discoumarols, chromanones, chromanols, isomers (e.g. cis/trans isomers) thereof, and mixtures thereof.

Preferred for use are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof. Flavonoid compounds useful herein are commercially available from a number of sources, e.g., Indofine Chemical Company, Inc., Stearloids, Inc., and Aldrich Chemical Company, Inc. The herein described flavonoid compounds are preferably present in from about 0.01% to about 20%, more preferably from about 0.1% to about 10%, and even more preferably from about 0.5% to about 5% by weight.

Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g. salts and esters).

The compositions may comprise a tanning active. When present, it is preferable that the compositions comprise from about 0.1% to about 20%, more preferably from about 2% to about 7% by weight of the composition. A preferred tanning active is dihydroxyacetone.

The compositions may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include niacinamide, kojic acid, arbutin, tranexamic acid, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract).

The compositions may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and even more preferably from about 0.05% to about 2% by weight of the composition.

Preferred examples of these actives include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cystein, lipoic acid, azelaic acid, arachidonic acid, benzoylperoxide, tetracycline, ibuprofen, naproxen, hydrocortisone, acetaminophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, climbazole, miconazole, ketoconazole, neocycin sulfate, and mixtures thereof.

The compositions may comprise a conditioning agent selected from the group consisting of humectants, moisturizers, or skin conditioners. A variety of these materials can be employed and each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol and hexylene glycol; polyethylene glycols; sugars and starch derivatives (e.g. alkoxylated glucose, fructose, sucrose, trehalose); hyaluronic acid; lactamide monoethanolamine; acetamide monoethanolamine; sucrose polyester; petrolatum; and mixtures thereof.

The cosmetic compositions of the subject invention include but are not limited to lotions, milks, mousses, serums, sprays, aerosols, foams, sticks, pencils, gels, creams and ointments. The compositions may also be applied via a woven or nonwoven synthetic and/or natural fibered textile (wipe or towelette).

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

Examples 1-4

The following are non-limiting examples of sunscreen compositions according to the present invention.

|  | Example | | | |
| --- | --- | --- | --- | --- |
|  | 1 | 2 | 3 | 4 |
| Phase A | | | | |
| Methyl Methacrylate Crosspolymer (Ganzpearl ® 0820) | 1.00 | 2.00 | 0.50 | 1.50 |
| Sylvaclear ™ PA 1200V and OMC Composite | 4.00 | 6.50 | — | — |
| Sylvaclear ™ AF 1900V and OMC Composite | — | — | 4.00 | 6.50 |
| Benzophenone-3 | 3.00 | 3.00 | 3.00 | 3.00 |
| Polymethylsilsequioxane | 4.00 | 4.00 | 4.00 | 4.00 |
| Cyclomethicone | 11.43 | 0.50 | 8.22 | 11.33 |
| Dimethicone PEG-10/15 Crosspolymer | 5.37 | 5.25 | 2.75 | 5.40 |
| Polyethylene wax | 3.54 | — | 2.41 | 2.05 |
| Fragrance | 0.10 | 0.10 | 0.10 | 0.10 |
| Titanium Dioxide (Coated With 5% Dimethicone) | — | — | — | 0.65 |
| Titanium Dioxide (Coated Mica Coated with 6% Methicone) | 5.00 | 0.01 | 1.00 | — |
| Phase B | | | | |
| Glycerin | 10.00 | 10.00 | 10.00 | 10.00 |
| Dexpanthenol | 0.50 | 0.50 | 0.50 | 0.50 |
| Pentylene Glycol | 3.00 | 3.00 | 3.00 | 3.00 |
| Hexamidine Disethionate | 0.10 | 0.10 | 0.10 | 0.10 |
| Niacinamide | 5.00 | 5.00 | 5.00 | 5.00 |
| Methylparaben | 0.20 | 0.20 | 0.20 | 0.20 |
| Ethylparaben | 0.05 | 0.05 | 0.05 | 0.05 |
| Sodium citrate | 0.20 | 0.20 | 0.20 | 0.20 |
| Citric Acid | 0.03 | 0.03 | 0.03 | 0.03 |
| Sodium Benzoate | 0.05 | 0.05 | 0.05 | 0.05 |
| Sodium Chloride | 0.50 | 0.50 | 0.50 | 0.50 |
| FD&C Red #40 (1%) | 0.05 | 0.05 | 0.05 | 0.05 |
| Water | Qs | Qs | Qs | Qs |

The formulas in the examples are prepared in a suitable container first by combining the ingredients of Phase A. In a separate suitable container, combine the ingredients of Phase B. Heat each phase to 73° C.-78° C. while mixing each phase using a suitable mixer (e.g. Anchor blade, propeller blade, IKA T25) until each reaches temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21° C. and 33° C.

Example 5

A series of comparative experiments were conducted to demonstrate aspects of the present invention. These experiments are based upon testing of the formulas outlined under Table I.

TABLE I

| INGREDIENT NAME | FORMULAS (Weight %) | | | | | | | | |
|---|---|---|---|---|---|---|---|---|---|
| | 1 | 2 | 3 | 4 | 5 | 6 | 7 | 8 | 9 |
| Phase A | | | | | | | | | |
| Water, deionized | 65.55 | 65.55 | 60.05 | 56.05 | 61.55 | 61.55 | 66.55 | 62.55 | 61.55 |
| Disodium EDTA | 0.10 | 0.10 | 0.10 | 0.10 | 0.10 | 0.10 | 0.10 | 0.10 | 0.10 |
| Glycerin | 5.00 | 5.00 | 5.00 | 5.00 | 5.00 | 5.00 | 5.00 | 5.00 | 5.00 |
| Phase B | | | | | | | | | |
| Promulgen D (Cetearyl Alcohol & Ceteareth 20) | 2.77 | 2.77 | 2.77 | 2.77 | 2.77 | 2.77 | 2.77 | 2.77 | 2.77 |
| PEG-100 Stearate | 1.85 | 1.85 | 1.85 | 1.85 | 1.85 | 1.85 | 1.85 | 1.85 | 1.85 |
| Parsol MCX ® (OMC) | 6.00 | — | — | — | — | — | — | — | — |
| Dermol MS ® (Caprylic/Capric Triglycerides) | 2.75 | 8.75 | 8.75 | 8.75 | 8.75 | 8.75 | 8.75 | 8.75 | 8.75 |
| Stearic Acid | 0.46 | 0.46 | 0.46 | 0.46 | 0.46 | 0.46 | 0.46 | 0.46 | 0.46 |
| Cholesterol | 0.92 | 0.92 | 0.92 | 0.92 | 0.92 | 0.92 | 0.92 | 0.92 | 0.92 |
| Phase C | | | | | | | | | |
| JTTO MS7 (Titanium Dioxide) | 2.00 | 2.00 | 2.00 | 2.00 | 2.00 | 2.00 | 2.00 | 2.00 | 2.00 |
| Phase D | | | | | | | | | |
| Permethyl 101A ® (Isohexadecane) | 0.50 | 0.50 | 0.50 | 0.50 | 0.50 | 0.50 | 0.50 | 0.50 | 0.50 |
| Phase G | | | | | | | | | |
| Aristoflex AVC ™ (Acryloyldimethyltaurate Copolymer) | 1.00 | 1.00 | 1.00 | 1.00 | 1.00 | 1.00 | 1.00 | 1.00 | 1.00 |
| Phase H | | | | | | | | | |
| DC 245 Fluid (Cyclopentasiloxane) | 8.50 | 8.50 | 8.50 | 8.50 | 8.50 | 8.50 | 8.50 | 8.50 | 8.50 |
| Ganzpearl GP 0820 ® (Methyl Methacrylate Crosspolymer) | 1.00 | 1.00 | 1.00 | 1.00 | 1.00 | 1.00 | — | — | 5.00 |
| UV Pearls ® | — | — | 5.50 | — | — | — | — | — | — |
| SunCaps 664 ® | — | — | — | 9.50 | — | — | — | — | — |
| Sylvaclear PA1200V ™ Composite (1:1 ratio OMC to polymer) | — | — | — | — | 4.00 | — | — | 4.00 | — |
| Sylvaclear PA 1200V ™ Polymer | — | — | — | — | — | 4.00 | — | — | — |
| Phase J | | | | | | | | | |
| Glydant Plus Liquid ™ (DMDM Hydantoin/Iodopropynyl Butylcarbamate) | 0.20 | 0.20 | 0.20 | 0.20 | 0.20 | 0.20 | 0.20 | 0.20 | 0.20 |
| Phase K | | | | | | | | | |
| Niacinamide | 0.10 | 0.10 | 0.10 | 0.10 | 0.10 | 0.10 | 0.10 | 0.10 | 0.10 |
| Water, deionized | 1.00 | 1.00 | 1.00 | 1.00 | 1.00 | 1.00 | 1.00 | 1.00 | 1.00 |
| Phase L | | | | | | | | | |
| Fragrance | 0.30 | 0.30 | 0.30 | 0.30 | 0.30 | 0.30 | 0.30 | 0.30 | 0.30 |
| Total | 100.00 | 100.00 | 100.00 | 100.00 | 100.00 | 100.00 | 100.00 | 100.00 | 100.00 |

Procedure:
1. Add Phase A to main beaker. Heat to 80° C. with mixing. Cool to 55-60 C.
2. Heat Phase B (oil phase) in side beaker to 80° C.
3. Add Phase C (JTTO-MS7) to Phase B and disperse using Homogenizer (splash guard down, 40 RPM, for 5 min).
4. Add Phases D, G and premix H to Phase B/C while mixing. Cool phase B/C/D/H/H to 55-60 C.
7. Transfer main beaker to homogenizer. Add Phase B/C/D/G/H to main beaker (Phase A) under homogenization. Homogenize for 1 minute with splash guard down at 40 RPM.
9. Transfer back to paddle mixing.
10. Add Phase J at 45° C. Continue mixing.
11. Premix Phase K and add at 40° C. Continue mixing.
12. Add Phase L at 40° C. Continue mixing.
13. Q/S DI water at 38° C. and mix until uniform.
14. Final Polish at 35° C. for 1 minute.

Optical Measurements

Opacity is the measure of intensity attenuation of a transmitted light beam shone perpendicular to a medium or film. The higher the direct beam attenuation, the greater will be the opacity. The source of the light beam attenuation is two fold: A) Some of the original light is reflected back from the film/medium. This gives the film/medium a true white/opaque appearance with great hiding power. Using pigment-grade $TiO_2$ in a formulation will give the effect. B) Some of the light is deflected from the straight beam path but still transmitted through the film/medium. In effect, the film/medium goes from being transparent to translucent, creating a "blurred" image. Another term for this is soft focus.

Procedure: Apply (or draw down) a 3 mil (76.2 μm) film of a formulation using a draw down bar on to a plastic overhead transparency sheet. Let the film dry for 2 hours at room temperature. Take the coated overhead transparency and place it in an Instrument Systems goniospectrophotometer. Set the light source and detector arrayed in a straight line perpendicular to the coated transparency. The light source (set at 209 million Watt-nm/cm$^2$, which serves as a reference for all Transmission Intensity Values reported herein) is turned on and the measurement of the transmitted light intensity is made. Further measurements are made by moving the detector 10, 30, 40, 50 degrees away from the direct transmission normal. These values indicate the extent of soft focus light scattering. To determine the extent of the intensity attenuation, compare the intensity value to that of an uncoated overhead transparency. The difference between these two values is the extent of the attenuation or opacity.

SPF Measurements

Sun protection factor (SPF) was measured in vitro using an Optometrics SPF 290 instrument. The test procedure required calibration of the monochrometer and sample stage of the Optometrics SPF 290 instrument. Thereafter the instrument was calibrated with a blank sample quartz plate (10 cm×10 cm and 3 mm thickness). Calibration zeros the UV detector. Formula is applied to a plate using an 1 mil draw-down applicator. This leaves a film of 2 mg/cm$^2$. The film is left to dry for 30 minutes. Subsequently an SPF reading is taken on the dried film using three measurements on different parts of the coated quartz plate and recording an average value.

Soft focus results for the formulas are reported in Table II.

and described in U.S. Pat. No. 5,733,531 herein incorporated by reference. These particles include octylmethoxycinnamate encapsulated in a binder that includes beeswax, carnauba wax, Vinyl Pyrrolidone/Eicosene Copolymer and emulsifiers. The encapsulates are supplied as an aqueous dispersion containing up to 65% solids.

Formula 5 represents the present invention wherein a Sylvaclear™ polymer sunscreen composite in combination with Ganzpearl® (porous polymethyl methacrylate particles) gives the highest Transmission Intensity Values within the Admissibility Range. Of particular note are the Transmission Intensity Values at the 30, 40 and 50 transmission angle measurements. Thus, Formula 5 compares favorably to Formulas 3 and 4 having alternate encapsulated sunscreen composites, namely UV Pearls® and SunCaps 664®. Formula 8 is identical to that of Formula 5 except that the Ganzpearl® (porous polymethyl methacrylate particles) is absent. A drastically lowered soft focus profile is found relative to that of Formula 5.

What is claimed is:
1. A cosmetic composition comprising:
 (i) from about 0.1 to about 20% by weight of composite particles formed of an organic sunscreen agent and a condensation polymerized polyamide which is a polyalkyleneoxypolyamide resin in a relative weight ratio of about 5:1 to about 1:10;
 (ii) from about 0.01 to about 10% by weight of water-insoluble powdered polymer formed as porous particles having an Oil Absorbance (castor oil) value ranging from about 90 to about 500 ml/100 gm; and
 (iii) a cosmetically acceptable carrier;

TABLE II

| | | | | | | | | 8 | | |
|---|---|---|---|---|---|---|---|---|---|---|
| | | | | | | 6 | | 4% | | |
| | 1 | | | 4 | 5 | 4% | 7 | Sylvaclear™ | 9 | Transmission |
| Variable | 6% | 2 | 3 | 9.5% | 4% | Sylvaclear™ | 0% OMC | Composite | 0% OMC | Intensity |
| Com- | External | 0% | 5.5% UV | Suncaps | Sylvaclear™ | (No | (No | (No | 5% | Admissibility |
| ponent | OMC | OMC | Pearls™ | 664™ | Composite | Sunscreen) | Ganzpear®) | Ganzpearl®) | Ganzpearl®) | Range |
| | | | | | Transmission Angle in Degrees | | | | | |
| 0 | 10.2 M | 10.1 M | 10.0 M | 10.2 M | 6.3 M | 6.1 M | 15.1 M | 8.6 M | 8.2 M | 4.0 to 7.0 million |
| 10 | 1.5 M | 1.5 M | 1.5 M | 1.5 M | 1.6 M | 1.7 M | 1.0 M | 1.6 M | 1.6 M | 1.0 to 2.0 million |
| 30 | 57K | 56K | 57K | 58K | 123K | 122K | 32K | 105K | 73K | 120 to 140 thousand |
| 40 | 30K | 31K | 31K | 32K | 62K | 61K | 25K | 50K | 41K | 60 to 80 thousand |
| 50 | 21K | 22K | 21K | 23K | 43K | 42K | 17K | 32K | 24K | 40 to 60 thousand |
| | | | | | SPF Value | | | | | |
| | 12 | 4 | 20 | 32 | 32 | 4 | 4 | 32 | 4 | |

*Values are the Intensity of light scatter (units are W-nm/cm2)

All the composites (UV Pearls®, SunCaps®, Sylvaclear™/Sunscreen) were formulated to deliver 2% octylmethoxycinnamate (OMC) to the overall cosmetic composition. UV Pearls® is sold by the Rona Division of EMD Chemicals. Their preparation is described in U.S. Pat. No. 7,264,795 herein incorporated by reference. UV Pearls® are sold as particulates dispersed in an aqueous carrier; the particulates are octylmethoxycinnamate coated with silica, polyvinylpyrrolidone and minor functional ingredients. SunCaps® are sold by Particle Sciences, Inc. of Bethlehem, Pa.

wherein the composition has a Transmission Intensity Value as follows:
 at a Transmission Angle of 0° ranging from 4.0 to 7.0 million W-nm/cm$^2$;
 at a Transmission Angle of 10° ranging from 1.0 to 2.0 million W-nm/cm$^2$;
 at a Transmission Angle of 30° ranging from 120 to 140 thousand W-nm/cm$^2$;
 at a Transmission Angle of 40° ranging from 60 to 80 thousand W-nm/cm$^2$; and at a Transmission Angle of 50° ranging from 40 to 60 thousand W-nm/cm$^2$.

2. The composition according to claim 1 wherein sunscreen agent and polyamide are intimately mixed together to form each of the composite particles.

3. The composition according to claim 1 wherein the composite particles have an average particle size ranging from about 10 to about 2,000 nm.

4. The composition according to claim 1 wherein the composite particles have an average particle size ranging from about 100 to about 1,500 nm.

5. The composition according to claim 1 wherein the sunscreen agent is octylmethoxycinnamate, Benzophenone-3 and mixtures thereof.

6. A composition according to claim 1 wherein the porous particles are polymethyl methacrylate.

7. A composition according to claim 1 wherein the particles are cross-linked.

8. The composition according to claim 1 wherein the composite particles have an average particle size ranging from about 200 to about 1000 nm.

9. The composition according to claim 1 wherein the relative weight ratio of organic sunscreen agent to condensation polymerized polyamide ranges from about 1:1 to about 1:3.

* * * * *